United States Patent [19]

Quesneau et al.

[11] Patent Number: 4,472,352
[45] Date of Patent: Sep. 18, 1984

[54] DEVICE FOR BIOCHEMICAL QUANTITATIVE ANALYSIS OF SUCCESSIVE SAMPLES

[75] Inventors: Richard Quesneau; Jean-Luc Berry, both of Compiegne, France

[73] Assignee: Biosys S.A., France

[21] Appl. No.: 423,847

[22] Filed: Sep. 24, 1982

[51] Int. Cl.³ .................... G01N 24/08; G01N 33/14
[52] U.S. Cl. ................................. 422/52; 422/64; 436/172; 435/291; 435/808
[58] Field of Search .................... 422/52, 64, 67; 435/291, 808; 356/244; 250/328, 364; 436/172

[56] References Cited

U.S. PATENT DOCUMENTS

| | | | |
|---|---|---|---|
| 3,520,660 | 7/1970 | Webb | 422/52 |
| 3,626,190 | 12/1971 | Cannon | 250/328 |
| 3,663,816 | 5/1972 | Scherzer et al. | 250/364 |
| 3,756,920 | 9/1973 | Kelbaugh et al. | 422/52 |
| 4,099,920 | 7/1978 | Heiss | 422/52 |
| 4,349,510 | 9/1982 | Kolemainen et al. | 422/52 |
| 4,366,118 | 12/1982 | Bunce et al. | 356/244 |

FOREIGN PATENT DOCUMENTS 2025609  1/1980  United Kingdom .
2056670  7/1980  United Kingdom .

*Primary Examiner*—Michael S. Marcus
*Assistant Examiner*—Joseph P. Carrier
*Attorney, Agent, or Firm*—Steinberg & Raskin

[57] ABSTRACT

The present invention relates to an automatic device for analyzing successive samples which comprises a turning plate provided at its periphery with vertical sockets containing a small tube filled with the sample to be analyzed, a photomultiplier arranged opposite the lateral face of the plate comprising an orifice communicating with the sockets, a first flat seal adapted to be actuated by a ring to be brought into contact with the lateral face of the plate, a second flat seal adapted to be actuated by another ring above the socket and a third seal carried by a movable cradle below the socket.

9 Claims, 3 Drawing Figures

DEVICE FOR BIOCHEMICAL QUANTITATIVE ANALYSIS OF SUCCESSIVE SAMPLES

BACKGROUND OF THE INVENTION

The present invention has essentially for a subject matter an automatic sequential device for quantitative analysis of samples following one another at a high rate and in which a luminescence reaction is produced by means of an appropriate reactant.

It is already known to inject into a sample to be measured an appropriate reactant to bring about therein a luminescence reaction which can be measured by means of apparatuses sensitive to relatively low light-intensities, such as for example photomultipliers, it being understood that the choice of the apparatus depends on the intensity of the luminescence to be measured and that the signal registered by the said apparatus can be amplified and treated by appropriate means of electronic analysis.

It is also known that luminescence reactions, especially bioluminescence reactions, are used for quantity determination of very small concentrations of reaction compounds. Since the light emitted is, in particular, proportional to the concentration of the compound present in the sample and since, generally, bioluminescence reactions produce very low light intensities, it is essential that the apparatus portion where the reaction and the measurement of the photons emitted take place be placed in complete darkness, i.e., sheltered from any external stray light, and this even before the beginning of the reaction and until after the end of the measurement.

Moreover, luminescence reactions generally develop very rapidly after the mixing of the reaction compounds, so that not only the mixing must be effected rapidly in a completely dark medium, but the measurement must also be performed in a totally dark medium, as soon as the first photons are emitted.

Up to the present, however, there has been proposed no automatic sequential combined injecting-measuring device in which the successive samples to be subjected to quantitative analysis are placed in complete darkness so as to allow instantaneous and accurate measurement of the very low and short-lived light intensities of the bioluminescence reactions, which, as is readily understood, is difficult to achieve when the measurement is to be effected on samples following one another at a high rate.

SUMMARY OF THE INVENTION

The purpose of the present invention is to fill in this gap by providing a new apparatus for quantitative analysis of successive samples, which allows the injection of the reactant into the sample as well as the measurement of the luminescence reaction to be effected in complete darkness, i.e., in the absence of any stray light, using to this end special light-tightness means, so that the measurement remains one of high accuracy and fidelity in the reproductibility of the results.

To this end, the invention has for a subject matter an automatic device for quantitative analysis of successive samples in which is produced a luminescence reaction by means of an appropriate reactant and which are arranged in sockets provided in proximity to the periphery of a turning plate with which is associated at least one luminescence measuring system arranged laterally opposite the periphery of the said plate, characterized in that is comprises light-tightness means, which are displaceable preferably simultaneously, and which are provided between the system of measurement and the periphery of the plate as well as on the upper and lower portions of the plate in the region of the socket containing the sample to be analysed.

According to a preferred form of embodiment, the aforesaid displaceable light-tight means are constituted by a first seal between the system of measurement and the periphery of the plate, adapted to be actuated by a ring externally concentric with the said measuring system, by a second seal adapted to be actuated by another ring externally concentric with the system of reactant injection arranged above the upper portion of the plate, and by a third seal resting on a cradle or the like adapted to be actuated vertically below the lower portion of the said plate.

It is therefore already understood that, when the sample carried by the plate will be located opposite the measuring system, the three seals can advantageously be applied to the plate, thus completely isolating from the external light the operation of reactant injection and the measurement of the luminescence reaction, the accuracy of which cannot thus be but excellent. Thereafter, in order to proceed to the measurement of the following sample on the plate, it will be sufficient to mechanically release the seals, thus allowing the rotation of the plate, to thereafter again apply the seal as described previously, in order to effect the measurement on the next sample.

According to another characterizing feature of the device of the invention, the ring actuating the aforesaid first seal is operated by bars or the like, themselves operated by a power cylinder and mounted hingedly on the said ring and the frame of the apparatus, whereas the other ring and the cradle actuating the aforesaid second and third seals, respectively, are rigidly connected to respective cross-members arranged above and below the plate.

The said two cross-members pertain to an assembly of two sets of movable cross-members actuated by one and the same power cylinder.

These two sets of cross-members are each mounted slidingly on the frame through the medium of spacers, the body of the last mentioned power cylinder being rigidly connected to one of the sets of cross-members, and the rod of the said power cylinder being rigidly connected to the other set of cross-members.

It will also be added here that one of the sets of cross-members, i.e., the one operating the aforesaid third seal is urged downwardly by springs, whereas the other set of cross-members, which operates the aforesaid second seal is urged upwardly, also by springs.

According to still another characterizing feature of the invention, the aforesaid first and second seals are constituted by flat seals, the first flat seal being rigidly connected to the end of a sheath or the like containing a photomultiplier, and the second flat seal being rigidly connected to the end of the reactant injection system, whereas the aforesaid third seal is constituted by a toric seal portion or O-ring portion which can be accommodated in an annular groove provided in the lower portion of the turning plate and opening into the aforesaid sockets for the sample.

According to still another characterizing feature of the invention, the cross-member actuating the ring which operates the second seal is provided with a pin for locking the movable plate, whereas the cross-member actuating the aforesaid third seal is provided with an orifice for the discharge of the receptacles after the analysis.

It should also be added that the aforesaid turning plate is provided with a circular rail for retaining the samples, arranged in the aforesaid annular groove but provided in the lower portion of the said plate.

It will also be noted that there are secured to the frame of the apparatus an assembly for distributing small tubular receptacles intended to contain the sample to be analysed, as well as reactant supply means connected to the aforesaid injection system.

It will be stressed here that the use of small, disposable receptacles for containing the samples, contributes to the accuracy of measurements made using the apparatus. Said apparatus according to the invention is particularly compact and allows accurate and easy handling of small amounts of reactants, which, as is known, are particularly expensive. In sum, therefore, the apparatus of the present invention allows accurate, continuous and rapid measurement in complete darkness, which it had never heretofore been possible to obtain with the presently known apparatuses.

BRIEF DESCRIPTION OF THE DRAWINGS

But other characterizing features and advantages of the invention will appear more clearly from the following detailed description with reference to the appended drawings, given solely by way of example and wherein.

DETAILED DESCRIPTION OF PREFERRED EMBODIMENTS

Figure 1:
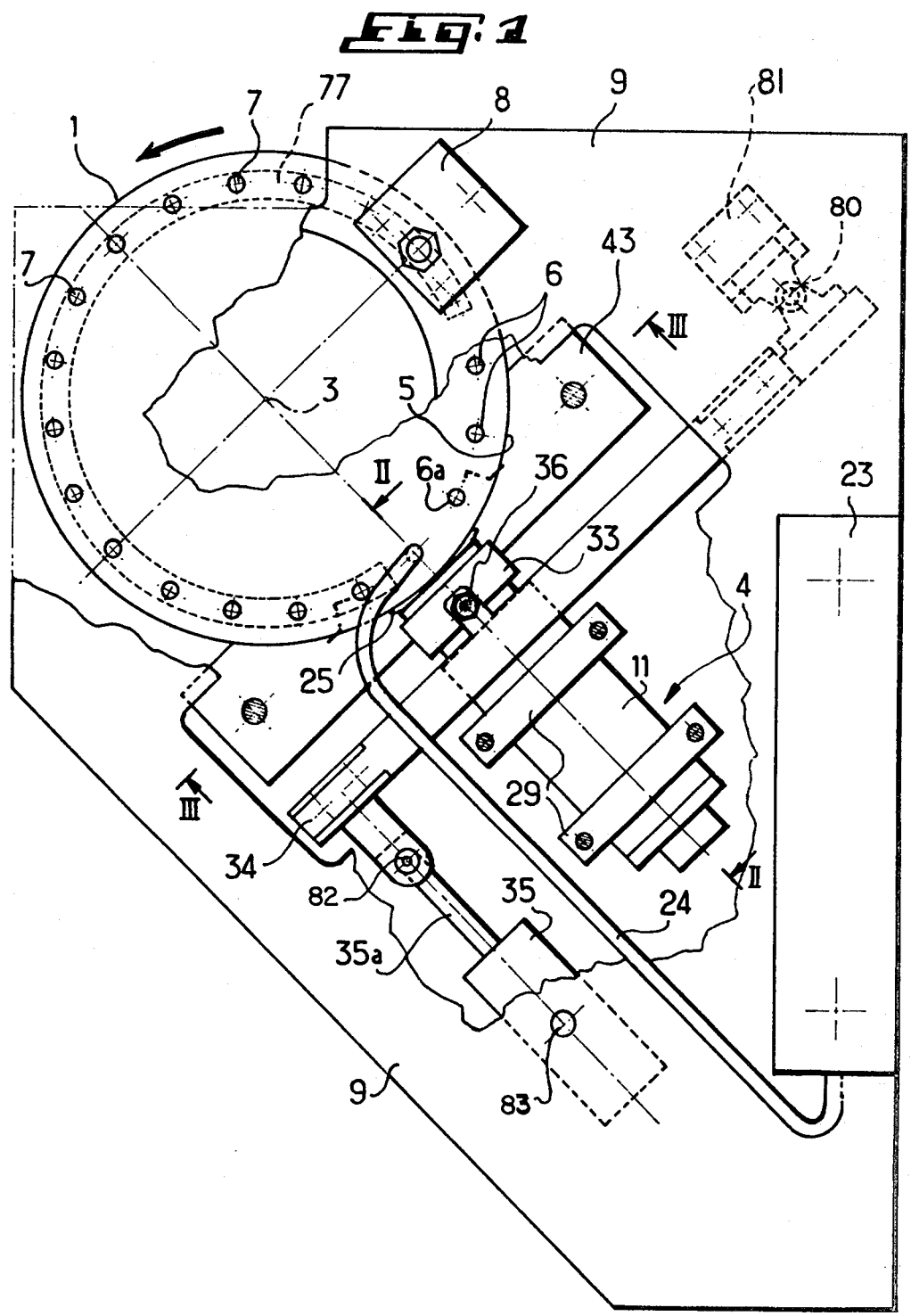
FIG. 1 is a diagrammatic, partially broken-away top view of an apparatus according to the principles of the invention.

According to an example of embodiment and referring to the appended drawings, a measuring device according to the invention comprises essentially a plate 1 rotatable about an axis 3 and with which is associated a system of measurement 4 arranged laterally opposite the edge 5 of the plate 1. The latter is provided in proximity to its periphery with regularly spaced vertical sockets 6 parallel with the axis 3, which sockets are intended to receive small tubes 7 filled with the sample to be analysed. At 8 in FIG. 1 is diagrammatically shown a unit for the distribution of receptacles or small tubes 7, which unit is secured to the supporting plate 9 forming the frame of the apparatus.

Each vertical socket 6 of the plate 1 opens onto the lateral face or edge 5 of the plate through the medium of an outwardly flared, frusto-conical orifice 10 coinciding with the axis of the system of measurement 4 which, here, is a photomultiplier 11, so that the said orifice 10 is located in proximity to the cathode 11a of the latter and completely encompasses the said cathode in its solid angle.

Each socket 6 also opens at 12 onto the upper portion 1a of the plate 1 and also onto the lower portion 1b of the plate 1 through the medium of an annular groove 13 the upper portion 13a of which is semi-toric in shape.

Figure 2:
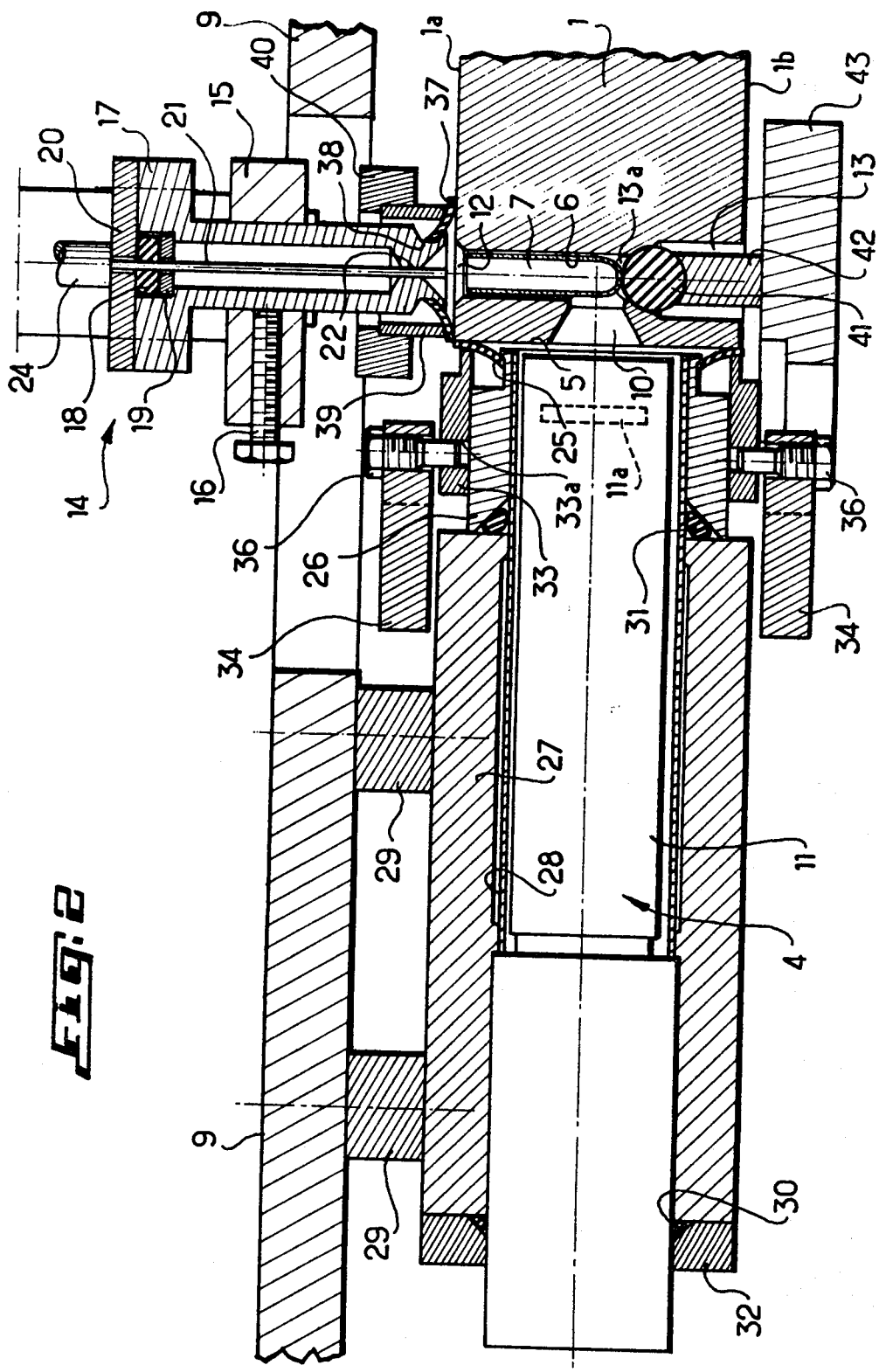
FIG. 2 is a sectional view taken upon the line II—II of FIG. 1.

As seen clearly in FIG. 2, a system 14 for the injection of reactant into the tubes 7 containing the sample is rigidly connected to the frame 9 through the medium of a general support 15 and is adjustable in height with respect to the latter by means of a lock screw 16. The system 14 overhangs the orifice 12 of the upper portion 1a of the plate 1 and is composed of needle support 17 provided at its upper portion with a seal 18 mounted on a bearing washer 19 and tightly held by a cover 20. The elements 18, 19 and 20 are drilled to allow the passage of a reactant injecting needle 21 the lower portion of which is guided by a narrowed portion 22 of the needle support 17. The needle 21 is supplied with reactant by appropriate injection means such as for example a syringe actuated by a piston, and shown diagrammatically at 23 in FIG. 1. The means 23 are rigidly assembled to the frame 9 and connected to the needle 21 through a tube or the like 24 which is deformable and opaque to light, which tube is seen in all three figures.

There will now be described one of the essential characterizing features of the invention, which consists in providing displaceable light-tight means between the photomultiplier 11 and the lateral periphery 5 of the plate 1 as well as on the upper face 1a of the plate 1 between this face and the reactant injection system 14, as also on the lower face 1a of the plate 1, i.e., at the lower portion of the socket 6 for the tubes 7. As will be seen, all these light-tight means advantageously allow the measuring cell constituted by the association of the photomultiplier 11 with any one of the sockets 6 to function in complete darkness for effecting the measurement of the luminescence reaction under ideal conditions.

To this end, the said light-tight means are essentially constituted by three seals which will not be described in detail.

A first flat seal 25 is provided between the photomultiplier 11 and the peripheral face 5 of the turning plate 1. The flat seal 25 is secured to a seal support 26 extending in prolongation of a sheath or the like 27 containing a photomultiplier 11. At 28 in FIG. 2 is seen an antimagnetic sleeve interposed between the sheath 27 and the photomultiplier 11. It will also be noted here that the photomultiplier assembly is connected to the frame 9 through the medium of spacers 29 and that the photomultiplier 11 and its associated antimagnetic sleeve are maintained by two O-rings 30, 31, respectively, tightly held by a rear plate 32 and the seal support 26.

On the seal support 26 is slidingly mounted a ring 33 adapted to bear upon the flat seal 25 so as to keep it in direct contact with the lateral face 5 of the turning plate 1 when the latter is stopped. This applied position of the flat seal 25 appears clearly in FIG. 2, it being understood that when the said seal is not acted upon by the ring 33, it remains out of contact with the face 5 of the turning plate.

As appears clearly in FIGS. 1 and 2, the ring 33 is actuated by bars or the like 34 operated by a power cylinder 35 and connected by screws 36 to the ring 33. More specifically and as clearly seen in FIG. 1, the bars 34 are hingedly connected at one of their ends at 80 to a stationary portion 81 secured to the frame 9, whereas the other end of the bars 34 is hingedly connected at 82 to the rod 35a of the power cylinder 35 secured at 83 to the frame 9. It will also be noted here that the screws 36 are preferably screwed into the crossbars 34 and have a teat-shaped end freely entering an opening 33a of the ring 33, thus providing a hinged connection of the bars 34 with the said ring.

Between the end of the reactant injection system 14 and the upper surface 1a of the plate 1 is provided a second flat seal 37 tightly mounted in a groove 38 provided at the said end of the injection system 14. Like the first flat seal 25, the second flat seal 37 at rest is out of contact with the upper surface 1a of the plate 1 (FIG. 3), but it can come into contact with the said surface owing to another bearing ring 39 externally concentric with the needle support 17. This ring is rigidly connected to a cross-member 40, the vertical actuation of which allowing the ring 39 to apply the seal 37 to the upper face 1a of the plate will be described later.

A third seal is provided at the bottom of the socket 6. This third seal shown at 41 is rigidly connected to a seal support forming a cradle 42 which is secured to a cross-member 43 which can be actuated vertically, as will be described later. This third seal 41 constitutes an O-ring portion the upper profile of while displays a semi-toric shape corresponding to the semi-toric shape 13a of the groove 13. It will be noted here that in the position of rest, the third seal 41 has no contact with the plate 1, whereas when the plate 1 is stopped the said seal bears upon the semi-toric shape 13a of the groove 13 to thus ensure light-tightness.

The cross-members 40 and 43 controlling the light-tightness at the upper portion 1 and at the lower portion 1b, respectively, of the plate 1 pertain to a movable assembly represented in FIG. 3 and comprising two sets 50 and 60 of movable cross-members actuated by one and the same power cylinder 70, as will now be described in detail.

Each set 50, 60 of movable cross-members is slidingly mounted in guiding sleeves 51 and 61 rigidly connected to the general support 15 and therefore to the frame 9.

More specifically, the set of cross-members 50 comprises the lower cross-member 43 and an upper cross-member 52 coupled by spacers 53 sliding in the sleeves 51.

The other set 60 of cross-members is made up of the lower cross-member 40 and an upper cross-member 62 coupled by spacers 63 sliding in sleeves 61. At 64 are shown bars secured to the upper cross-member 62 and sliding at 65 in the orifices of a small spacer 67 between the guiding sleeves 61. Around each bar 64 is provided a spring 66 which urges upwardly the set 60 of cross-members 62, 40.

There is also provided a spring 54 around the spacers 53 between the lower cross-member 43 and the stationary support 15, so as to constantly urge the set 50 of cross-members 43, 52 downwardly.

The body 71 of the vertical power cylinder 70 is secured to the cross-member 52, whereas the rod 72 of this power cylinder is secured to the cross-member 62.

Figure 3:
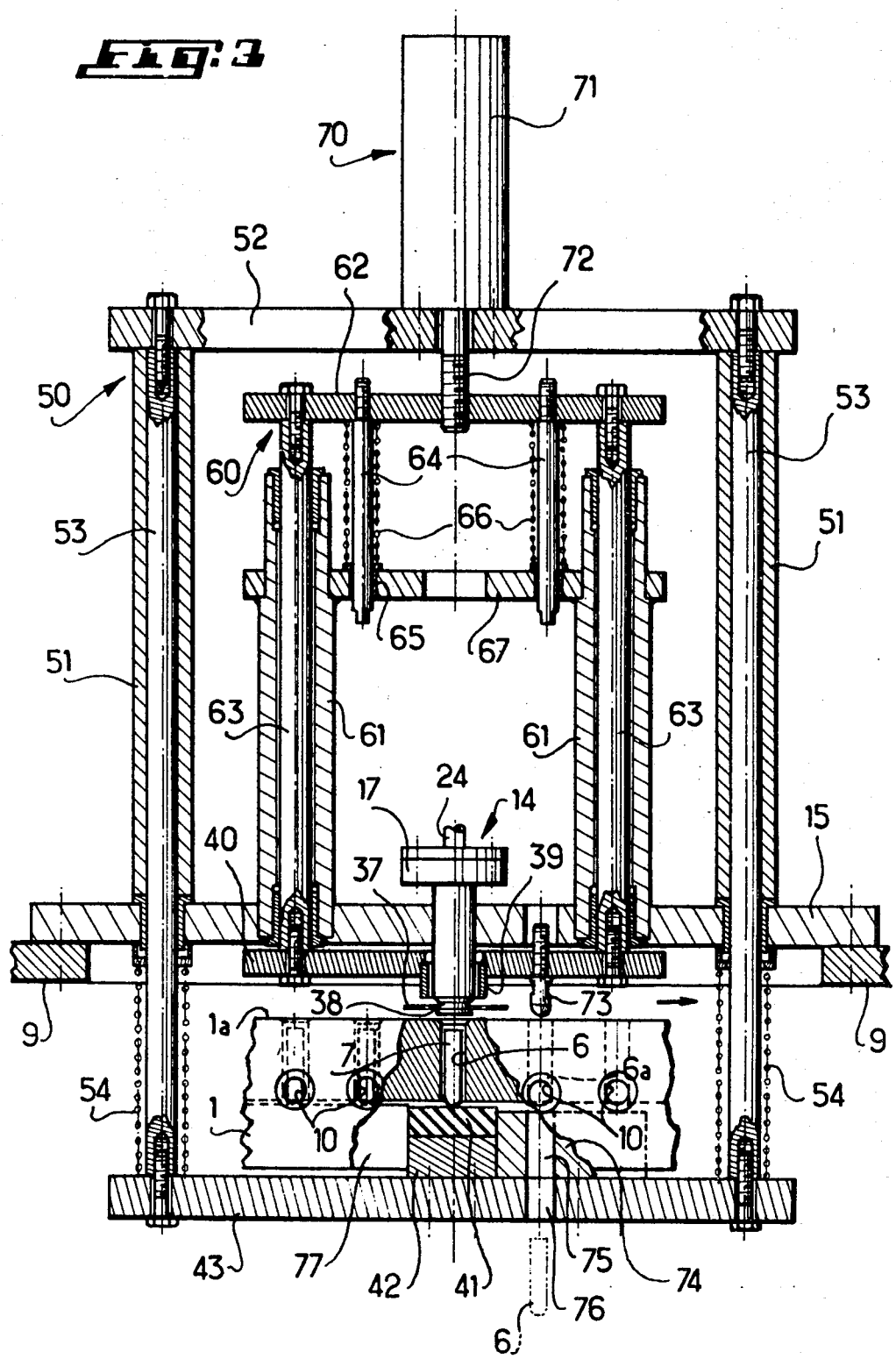
FIG. 3 is another sectional view taken substantially upon the line III—III of FIG. 1.

It is therefore understood that in the maximum spaced-apart position of the cross-members 40 and 43 under the action of the springs 66 and 54 corresponds a position of the seals 37 and 41 which is normal, i.e. the said seals are not applied to the turning plate 1, as seen clearly in FIG. 3. On the contrary, when the power cylinder 70 is actuated, its rod 72 pushes the assembly 60 and therefore the ring 39 carried by the lower cross-member 40 against the seal 37 which will thus be tightly applied against the upper face 1a of the plate 1, and at that moment, as a result of the reaction, the movable assembly 50 will rise against the action of the springs 54 to apply the semi-toric seal 41 against the bottom of the sockets 6 containing the sample support tube 7. In other words, the combination of the descending and ascending movements of sub-assemblies 60 and 50 will ensure an almost simultaneous light-tightness on both sides of the turning plate 1 in the region of the socket 6.

At 73 in FIG. 3 is shown a pin for locking the movable plate 1, which pin is rigidly connected to the lower cross-member 40 and can enter a socket 6a adjacent to the socket 6 containing a sample ready to be analysed.

The lower cross-member 43 carries a seal abutment 74 provided with a hole 75 vertically coinciding with a corresponding hole 76 provided in the said cross-member and allowing the discharge of the tubes 6 after their passage through the measuring cell.

As seen in FIGS. 1 and 3, the turning plate 1 is provided with a circular rail 77 arranged in an annular groove 13 provided at the lower portion 1b of the said plate. The rail 77 is not in contact with the plate 1 and is provided between the assembly 8 for the distribution of the receptacles 7 and the immediate upstream region of the toric portion of the seal 41, thus allowing the receptacles or the tubes 7 to be retained within the sockets 6.

It will also be added here that the assembly 8 for the distribution of the receptacles 7 is connected upstream to a supply system (not shown) which supplies the receptacles one by one, the latter being of course transparent and advantageously in the shape of small testing tubes which are presented with their opening directed upwardly. It is of course understood that the distributing assembly may be designed by any appropriate means.

There will now be described the operation of the device of the invention in the light of the foregoing description.

The plate 1 is driven in rotation in the direction of the arrow seen in FIG. 1 by any appropriate means, such as for example an electric motor and a coupling (not shown).

When the seals 25, 37 and 41 are at rest, as seen in FIG. 3, the coupling drives the motor which rotates the plate permanently.

When the plate reaches a suitable stopped position, i.e., when a socket 6 is in a position of coaxial alignment with the needle 21 and therefore with the photomultiplier 11, a detector (not shown) ensures the uncoupling of the plate, thus causing the latter to stop.

The power cylinder 70 is immediately actuated, thus ensuring the locking of the plate 1 in a suitable position through the medium of the pin 73 which enters the upper portion of a socket 6a. As a result, power cylinder 70 produces a double and reversed displacement of the sub-assemblies 60 and 50, as explained previously, so that the bearing ring 39 presses the seal 37 against the upper surface 1a of the plate and the cross-member 43 presses the toric portion of the seal 41 against the semi-toric shape 13a of the annular groove 13. In short, the double movement of the sub-assemblies 60 and 50 ensures absolute light-tightness at the upper and lower ends of the socket 6 containing the sample to be analysed.

Simultaneously, the power cylinder 35 actuates the transverse bars 34 so as to compress the flat seal 25 by means of the bearing ring 33, thus ensuring the light-tightness of the lateral face of the measuring cell.

The conditions for proper analysis of the luminescence are thus ensured, but it should be noted here that the analysis takes place only if the cell contains a tube 70 loaded with a sample to be analysed. To this end, the injection assembly 23 is actuated and supplies through the tube 24 and the needle 21 an accurate amount of reactant into the tubes 7. Thereafter the bioluminescent reaction will develop within the sample contained in the tubes 7 and the light emitted by the reaction passes through the frusto-conical aperture 10 to energize the cathode 11a of the photomultiplier 11, whose signal will be amplified and treated by an appropriate electronic system (not shown).

When the measurement is completed, the power cylinders 70 and 35 are actuated in the opposite direction to release the seals 37, 41 and 25 and also disengage the lock pin 73. The coupling is again energized and the plate 1 begins rotating until the next socket 6 reaches a position suitable for a further stoppage. At the same time, the socket 6a which contained the receptacle 7 having been subjected to a measurement then stops in a vertically coinciding position with respect to the orifices 75 and 76, thus allowing automatic discharge by simple gravity of the receptacle 7 since the circular rail 77 is interrupted at that level (FIG. 3).

There is therefore obtained according to the invention an entirely automated device allowing measuring cells completely tight to external light to be obtained, such cells being obtained successively and almost instantaneously, since the transfer which consists in un-tightening the sealing system, in passing to the following socket and in tightening the sealing system lasts only a few seconds. It is therefore understood that the invention allows measurements to be effected successively at a high rate and with the highest possible accuracy and reliability.

Of course, the invention is by no means limited to the form of embodiment described and illustrated which has been given by way of example only.

Thus, for example, without departing from the scope of the invention, use can be made of any number of power cylinders to obtain the light-tightness according to the principles of the invention. Also, other accessories can be used, such as for example obturators placed before the aperture of the photomultiplier.

The invention, therefore, comprises all technical means equivalent to the means described as well as their combinations, should the latter be carried out according to its gist and used within the scope of protection claimed.

What is claimed is:

1. An automatic sequential apparatus for quantitative analysis of successive samples carried in tubes and in which a luminescence reaction is produced by means of an appropriate reactant, said apparatus comprising the combination of:

a frame;
   a plate rotatably mounted on said frame and provided proximate to its periphery with regularly spaced vertical sockets adapted to receive the tubes filled with the samples to be analyzed,
   each socket comprising a lateral opening, an upper opening, and a lower opening which respectively open onto a peripheral face, an upper face, and a lower face of said plate, said lateral opening exposing only a portion of a tube;
   luminescence analyzing means arranged laterally opposite the peripheral face and lateral opening of said plate;
   first displaceable ring means externally concentric with said analyzing means, and
   first seal means engaged with, and adapted to be actuated by, said first ring means for sealing the lateral opening to ensure light tightness between said analyzing means and the peripheral face of said plate;
   a reactant injection assembly arranged above the upper face of said plate opposite the upper opening thereof;
   second displaceable ring means externally concentric with said injection assembly, and
   second seal means engaged with, and adapted to be actuated by, said second ring means for sealing the upper opening to ensure light tightness between said injection assembly and the upper face of said plate;
   cradle means disposed, and adapted to be substantially vertically actuated, below the lower face of said plate, and
   third seal means rigidly connected to said cradle means opposite the lower opening and adapted to be actuated by said cradle means to seal the lower opening to ensure light tightness of the same upon vertical displacement of said cradle means; and
   stationary substantially circular rail means provided within the lower opening for retaining the tubes in the respective sockets during one part of a rotational path of travel of said tubes with said plate, before the tubes reach said analyzing means.

2. An apparatus according to claim 1, wherein
   said first and second seal means each comprise flat seals,
   said flat seal of said first seal means being rigidly connected with the ends of a sheath containing a photomultiplier, and
   said flat seal of said second seal means being rigidly connected with an end of said reactant injection assembly, and
   said third seal means is constituted by an O-ring portion entering the lower opening provided in the lower face of said plate, and opening into the sockets for the tubes.

3. An apparatus according to claim 1, wherein the lower opening in said plate is in the form of an annular groove.

4. An apparatus according to claim 1, additionally comprising
   a unit secured to said frame for the distribution of the tubes in the sockets within said plate, and
   reactant supply means connected with said injection assembly and secured to said frame.

5. An apparatus according to claim 1, comprising
   bar means for actuating said first ring means and hingedly mounted on said first ring means and on said frame; and
   a pair of cross-members, one of said pair arranged above said plate and the other of said pair arranged below said plate, a respective one of said cross-members connected with said second ring means and adapted to actuate the same, and a respective other of said cross-members connected with said cradle means and adapted to actuate the same.

6. An apparatus according to claim 5, further comprising:
   a first power cylinder for actuating said bar means and engaged with the same;
   two sets of movable cross-members, each supporting a respective one of said pair of cross-members; and
   a second power cylinder for actuating said two sets of cross-members and engaged with the same.

7. An apparatus according to claim 6, wherein said both sets of cross-members comprise respective spacers slidingly mounted on said frame, and
said second cylinder comprises
a body rigidly connected to one of said sets of cross-members, and
a rod rigidly connected to said other set of said sets of cross-members.

8. An apparatus according to claim 6, further comprising:
first spring means engaged with said one of said sets of cross-members adapted to actuate said third seal means, and adapted to urge said respective set of cross-members downwardly, and
second spring means engaged with said other set of cross-members adapted to actuate said second seal means, and adapted to urge said other set of cross-members upwardly.

9. A device according to claim 5, wherein said cross-member adapted to actuate said second ring means which, in turn, is adapted to actuate said second seal means, is provided with a pin adapted to lock said plate, and
said cross-member adapted to actuate said third seal means is provided with an orifice for the discharge of the tubes.

* * * * *